(12) United States Patent
Rimshnick

(10) Patent No.: US 12,431,225 B2
(45) Date of Patent: Sep. 30, 2025

(54) IDENTIFYING COMMON CARE GAPS BETWEEN PATIENT GROUPS

(71) Applicant: CVS Pharmacy, Inc., Woonsocket, RI (US)

(72) Inventor: David Rimshnick, Mineola, NY (US)

(73) Assignee: CVS PHARMACY, INC., Woonsocket, RI (US)

( * ) Notice: Subject to any disclaimer, the term of this patent is extended or adjusted under 35 U.S.C. 154(b) by 243 days.

(21) Appl. No.: 17/569,692

(22) Filed: Jan. 6, 2022

(65) Prior Publication Data

US 2022/0215913 A1 Jul. 7, 2022

Related U.S. Application Data

(60) Provisional application No. 63/134,653, filed on Jan. 7, 2021.

(51) Int. Cl.
*G16H 15/00* (2018.01)
*G16H 10/60* (2018.01)
*G16H 20/10* (2018.01)

(52) U.S. Cl.
CPC .............. *G16H 10/60* (2018.01); *G16H 15/00* (2018.01); *G16H 20/10* (2018.01)

(58) Field of Classification Search
None
See application file for complete search history.

(56) References Cited

U.S. PATENT DOCUMENTS

| | | | |
|---|---|---|---|
| 6,802,810 B2 * | 10/2004 | Ciarniello | G16H 50/30 600/300 |
| 2009/0076857 A1 * | 3/2009 | Eletreby | G16H 70/40 705/2 |
| 2009/0125333 A1 * | 5/2009 | Heywood | G06Q 50/22 705/2 |
| 2015/0066536 A1 * | 3/2015 | Spates | G06F 16/36 705/3 |
| 2015/0112700 A1 * | 4/2015 | Sublett | G16H 40/20 705/2 |
| 2016/0357910 A1 * | 12/2016 | Ghouri | G16H 10/60 |
| 2020/0335224 A1 * | 10/2020 | Sreenivasan | G16H 40/20 |

* cited by examiner

*Primary Examiner* — John A Pauls
(74) *Attorney, Agent, or Firm* — Sheridan Ross PC

(57) ABSTRACT

A system and method are described for analyzing electronic data records received from a patient database. Analyzing the electronic data records may include identifying one or more common care gaps shared between a group of patients having a common value in a data field of the patient's corresponding electronic data record. The identification of the common care gap can be used to identify treatments that are not being provided to the group of patients, but should be provided to the group of patients.

20 Claims, 7 Drawing Sheets

IDENTIFYING COMMON CARE GAPS BETWEEN PATIENT GROUPS

CROSS REFERENCE TO RELATED APPLICATION

The present application claims the benefit of and priority under 35 U.S.C. § 119(e) to 63/134,653, filed on Jan. 7, 2021, the entire disclosure of which is hereby incorporated by reference.

FIELD OF THE DISCLOSURE

The disclosure relates to systems and methods for obtaining, analyzing, and reporting on patient data records in a secure and actionable fashion.

BACKGROUND

Pharmaceutical developers, healthcare providers, pharmaceutical distributors, and other entities involved in the delivery of treatments to patients are able to observe historical information related to such treatments. For instance, pharmaceutical developers and distributors have vast amounts of data related to sales of pharmaceutical products. Similarly, healthcare providers can access treatment histories for their patients. The historical information related to treatments actually delivered to a patient can help guide future decisions for patients and their healthcare providers. What is less apparent to pharmaceutical developers, healthcare providers, pharmaceutical distributors, patients, and other entities, however, is what patients should be receiving a particular treatment, but are not.

SUMMARY

It is with respect to the above-noted shortcomings that an improved patient data analysis approach is desired. Specifically, example solutions described herein build upon a healthcare management system that provides a clinically sophisticated, comprehensive solution to improve the quality and manage the costs of patient care. Where past healthcare management systems are only backward looking and focused on events that have actually occurred, the proposed healthcare management systems described herein are able to identify common care gaps for patients or patient groups, meaning that actions can be driven based on treatments that have not been or should be provided to a patient or patient groups. By analyzing patient data in a unique and targeted manner, the healthcare management systems described herein allow pharmaceutical developers, healthcare providers, pharmaceutical distributors, patients, and the like to better understand what future healthcare actions can be taken based on care gaps identified in historical patient data.

In one aspect, a system is provided that includes: a processor and computer memory coupled with the processor, where the computer memory includes data stored thereon that enables the processor to: receive electronic data records from a patient database, where each of the electronic data records includes patient data and treatment data corresponding to a patient; analyze the electronic data records for common care gaps shared between a group of patients having a common value in a data field of the patient's corresponding electronic data record; determine a common care gap exists for the group of patients; map the common care gap to the common value in the data field; generate a report that identifies the common care gap and the common value in the data field; and transmit the report to a communication device of an entity having an ability to provide treatment for the common care gap.

Examples may include one of the following features, or any combination thereof. The entity having the ability to provide the treatment for the common care gap may correspond to a healthcare provider, a pharmaceutical developer, a pharmaceutical distributer, combinations thereof, and the like. The entity having the ability to provide the treatment for the common care gap may alternatively or additionally correspond to the patient themselves.

In some examples, analyzing the electronic data records for common care gaps may include applying a set of matrices to the electronic data records, where each matrix in the set of matrices contains a plurality of defined elements that incorporate medical treatment information for the patient from at least one healthcare provider, and where an identifier of the at least one healthcare provider corresponds to the common value in the data field.

In some examples, the common care gap may include an anomalous data occurrence or number of anomalous data occurrences for a group of patients as compared to other patients not belonging to the group. For instance, the anomalous data occurrence may correspond to an absence of a pharmaceutical treatment for patients in the group of patients while the pharmaceutical treatment is provided to patients outside of the group of patients.

In some examples, the common care gap may correspond to a gap in a pharmaceutical treatment, where the treatment data includes an identifier of a prescribed medicament in the pharmaceutical treatment, and where the entity includes a pharmaceutical developer. Alternatively or additionally, the common care gap may correspond to a therapeutic treatment, where the treatment data includes an identifier of a prescribed therapy in the therapeutic treatment, and where the entity includes a healthcare provider.

In some examples, the report may include a data file that aggregates the electronic data records for the patients in the group of patients and the report anonymizes the patient data to remove sensitive information prior to transmitting the report.

In some examples, the electronic data records may include a plurality of data fields describing the treatment data, where the plurality of data fields include one or more of a laboratory test results data field, a prescription drug data field, a health plan claims data field, a provider data field, and an in-patient information data field. The provider data field may correspond to the data field having the common value and the common value may include an identifier of the entity. Alternatively or additionally, the plurality of data fields may further include a location data field, where the location data field corresponds to the data field having the common value, and where the common value includes an identifier of a geographic area.

In some examples, the processor may also be enabled to transmit a database query to the patient database, where the database query includes at least one of an identifier of the entity, an identifier of a prescription drug, and a location identifier, and where the group of patients correspond to patients that include an electronic data record that satisfies the database query.

In another aspect, a method of identifying and reporting on care gaps is provided that includes: receiving, from a patient database, electronic data records comprising patient data and treatment data corresponding to a patient; analyzing, with a processor, the electronic data records for common care gaps shared between a group of patients having a common value in a data field of the patient's corresponding electronic data record; determining, with the processor, that a common care gap exists for the group of patients; mapping, with the processor, the common care gap to the common value in the data field; generating, with the processor, a report that identifies the common care gap and the common value in the data field; and causing the report to be transmitted to a communication device of an entity having an ability to provide treatment for the common care gap.

In another aspect, a system is provided that includes: a processor and a computer memory coupled with the processor, where the computer memory includes data stored thereon that enables the processor to: analyze health data records associated with subjects in a patient member group for health deficiency indicators; identify, based on the analysis of the health data records, a subset of the subjects in the patient member group having a common health deficiency; determine whether the health data records include a previously prescribed treatment for each subject in the subset of the subjects in the patient member group, the previously prescribed treatment associated with the common health deficiency; group subjects of the subsets in the patient member group having a same previously prescribed treatment associated with the common health deficiency into discrete groups; determine a difference between treatments for each group of the discrete groups; generate a report including information about the difference between treatments; and send, across a communications network, the report to a communication device of an entity having an ability to provide treatment to at least one subject from at least one of the discrete groups.

Examples may include one of the following features, or any combination thereof. The computer memory may further include data stored thereon that enables the processor to receive the health data records associated with the subjects in the patient group prior to analyzing the health data records.

In some examples, the prescribed treatment may include at least one of a prescribed medicament and a prescribed therapy.

In some examples, the entity corresponds to a pharmaceutical developer of the prescribed medicament.

In some examples, patient member information in the report is anonymized removing personally identifiable information about the subjects in the patient member group.

In some examples, the computer memory further includes data stored thereon that enables the processor to: determine an efficacy of treatment for each group of the discrete groups and determine a highest efficacy treatment from the efficacy of treatment for each group of the discrete groups.

In another aspect, a method is provided that includes: analyzing health data records associated with subjects in a patient member group for health deficiency indicators; identifying, based on the analysis of the health data records, a subset of the subjects in the patient member group having a common health deficiency; determining whether the health data records include a previously prescribed treatment for each subject in the subset of the subjects in the patient member group, the previously prescribed treatment associated with the common health deficiency; grouping subjects of the subsets in the patient member group having a same previously prescribed treatment associated with the common health deficiency into discrete groups; determining a difference between treatments for each group of the discrete groups; generating a report including information about the difference between treatments; and sending, across a communications network, the report to a communication device of an entity having an ability to provide treatment to address the common health deficiency.

All examples and features mentioned above can be combined in any technically possible way.

BRIEF DESCRIPTION OF THE DRAWINGS

The present disclosure is described in conjunction with the appended figures, which are not necessarily drawn to scale.

DETAILED DESCRIPTION

Before any examples of the disclosure are explained in detail, it is to be understood that the disclosure is not limited in its application to the details of construction and the arrangement of components set forth in the following description or illustrated in the following drawings. The disclosure is capable of other configurations and of being practiced or of being carried out in various ways. Also, it is to be understood that the phraseology and terminology used herein is for the purpose of description and should not be regarded as limiting.

Figure 1:
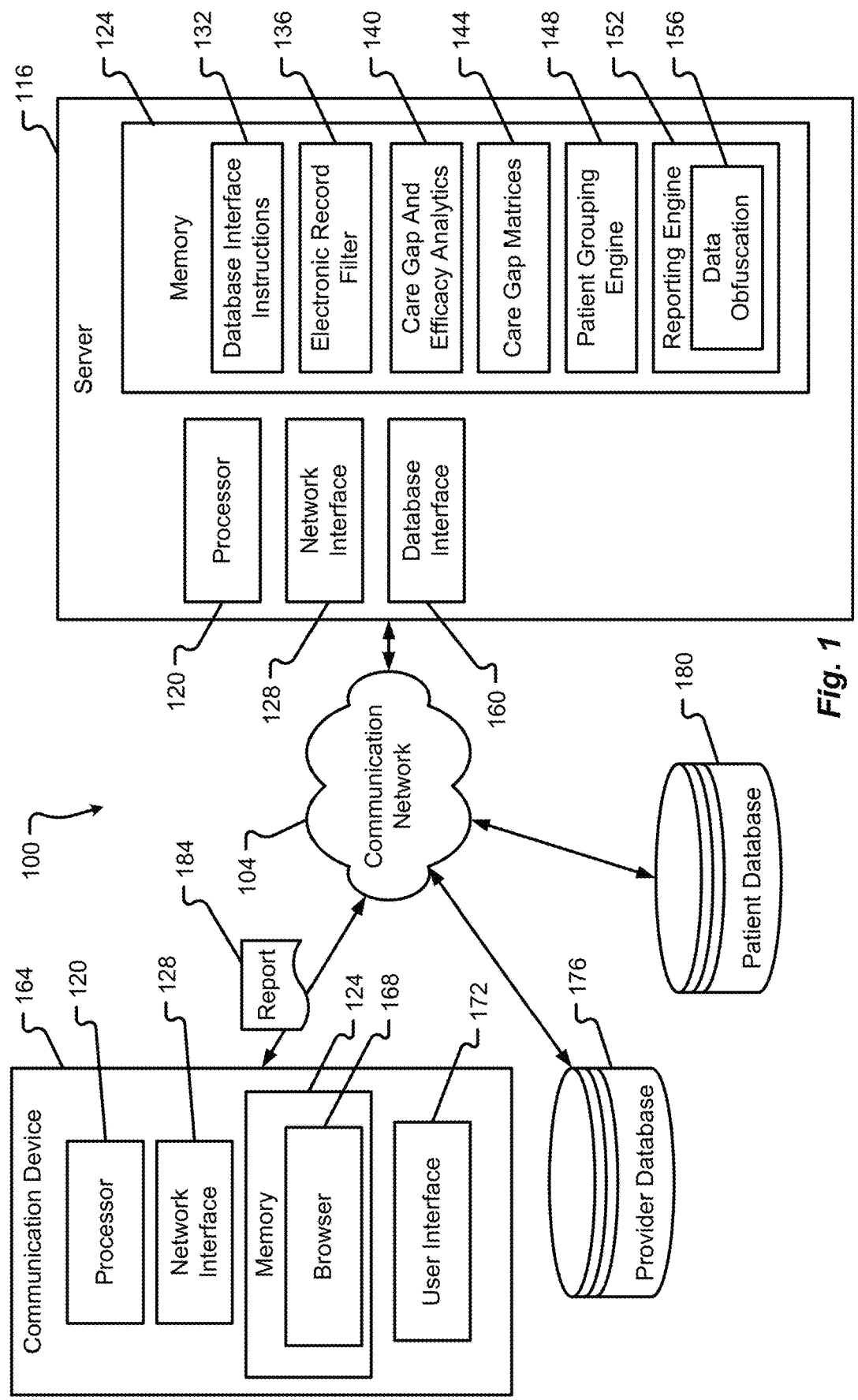
FIG. 1 is a block diagram depicting a system in accordance with at least some examples of the present disclosure.

With reference now to FIG. 1, an example system 100 will be described. The system 100, in some examples, may include one or more computing devices operating in cooperation with one another to provide care gap analytics capabilities. The components of the system 100 may be utilized to facilitate one, some, or all of the methods described herein or portions thereof without departing from the scope of the present disclosure. Furthermore, although particular servers are depicted as including particular components or instruction sets, it should be appreciated that examples of the present disclosure are not so limited. For instance, a single server may be provided with all of the instruction sets and data depicted and described in the server of FIG. 1. Alternatively, different servers may be provided with different instruction sets than those depicted in FIG. 1.

The system 100 is shown to include a communication network 104 that facilitates machine-to-machine communications between a server 116, one or more communication devices 164, and/or one or more databases 176, 180.

The communication network 104 may include any type of known communication medium or collection of communication media and may use any type of protocols to transport messages between endpoints. The communication network 104 may include wired and/or wireless communication technologies. The Internet is an example of the communication network 104 that constitutes an Internet Protocol (IP) network consisting of many computers, computing networks, and other communication devices located all over the world, which are connected through many telephone systems and other means. Other examples of the communication network 104 include, without limitation, a standard Plain Old Telephone System (POTS), an Integrated Services Digital Network (ISDN), the Public Switched Telephone Network (PSTN), a Local Area Network (LAN), a Wide Area Network (WAN), a Session Initiation Protocol (SIP) network, a Voice over Internet Protocol (VoIP) network, a cellular network, and any other type of packet-switched or circuit-switched network known in the art. In addition, it can be appreciated that the communication network 104 need not be limited to any one network type, and instead may be comprised of a number of different networks and/or network types. Moreover, the communication network 104 may comprise a number of different communication media such as coaxial cable, copper cable/wire, fiber-optic cable, antennas for transmitting/receiving wireless messages, and combinations thereof.

The communication device 164 may correspond to any type of computing resource that includes a processor 120, computer memory 124, and a user interface 172. The communication device 164 may also include one or more network interfaces 128 that connect the communication device 164 to the communication network 104 and enable the communication device 164 to send/receive packets via the communication network 104. Non-limiting examples of communication devices 164 include personal computers, laptops, mobile phones, smart phones, tablets, etc. In some examples, the communication device 164 is configured to be used by and/or carried by a human user. As will be discussed in further detail herein, a user or entity associated with a communication device 164 may be involved in some aspect of patient care. For instance, the communication device 164 may be associated with a healthcare provider, a pharmaceutical developer, a pharmaceutical distributor, combinations thereof, and the like. Although not depicted, the system 100 may include a number of different communication devices 164, each of which are associated with different entities.

To facilitate use of the communication device 164 and to enable a user thereof to view a report 184 received from the server 116 at the communication device 164, the memory 124 may store a browser 168 or other type of application that enables the communication device 164 to render a presentation (e.g., visual, audible, etc.) of the report 184 via a user interface 172 of the communication device 164. In some examples, the browser 168 may be configured to receive the report 184 in an electronic format and present content of the report 184 via the user interface 172.

The server 116 is shown to include a processor 120, memory 124, and network interface 128. These resources of the server 116 may enable functionality of the server 116 as will be described herein. For instance, the network interface 128 provides the server 116 with the ability to send and receive communication packets over the communication network 104. More specifically, the network interface 128 may enable the server 116 to provide database queries to the various databases 176, 180 of the system 100, receive responses to the database queries, transmit a report 184 to communication devices 116 of the system 100, and otherwise communicate with devices via the communication network 104. The network interface 128 may be provided as a network interface card (NIC), a network port, drivers for the same, and the like. Communications between the components of the server 116 and other devices connected to the communication network 104 may all flow through the network interface 128.

The processor 120 may correspond to one or many computer processing devices. For instance, the processor 120 may be provided as silicon, as a Field Programmable Gate Array (FPGA), an Application-Specific Integrated Circuit (ASIC), any other type of Integrated Circuit (IC) chip, a collection of IC chips, or the like. As a more specific example, the processor 120 may be provided as a microprocessor, Central Processing Unit (CPU), Graphics Processing Unit (GPU), Data Processing Unit (DPU), or plurality of microprocessors that are configured to execute the instructions sets stored in memory 124. Upon executing the instruction sets stored in memory 124, the processor 120 enables various functions of the server 116. The processor 120 may also be configured to utilize data stored in memory 124 as a neural network or other machine learning (ML) architecture. Thus, while certain elements stored in memory 124 may be described as instructions or instruction sets, it should be appreciated that functions of the server 116 may be implemented using ML techniques.

The memory 124 may include any type of computer memory device or collection of computer memory devices. Non-limiting examples of memory 124 include Random Access Memory (RAM), Read Only Memory (ROM), flash memory, Electronically-Erasable Programmable ROM (EEPROM), Dynamic RAM (DRAM), etc. The memory 124 may be configured to store the instruction sets, neural networks, and other data structures depicted in addition to temporarily storing data for the processor 120 to execute various types of routines or functions.

The illustrative data or instruction sets that may be stored in memory 124 include, without limitation, database interface instructions 132, an electronic record filter 136, a care gap and efficacy analytics engine 140, care gap matrices 144, a patient grouping engine 148, and a reporting engine 152. In some examples, the reporting engine 152 may include data obfuscation capabilities 156 that enable the reporting engine 152 to obfuscate, remove, redact, or otherwise hide personally identifiable information (PII) from a report 184 prior to transmitting the report 184 to a communication device 116.

In some examples, the database interface instructions 132, when executed by the processor 120, may enable the server 116 to send data to and receive data from a provider database 176 and/or a patient database 180. For instance, the database interface instructions 132 may be configured to generate database queries, allow system administrators to define database queries, transmit database queries to the database (s) 176, 180, receive responses to database queries, and format responses received from the databases for processing by other components of the server 116.

The electronic record filter 136 may also be used in connection with processing data received from the various databases 176, 180. For instance, the electronic record filter 136 may be leveraged by the database interface instructions 132 to filter or reduce the number of electronic records provided to a care gap and efficacy analytics engine 140. Specifically, but without limitation, the database interface instructions 132 may receive a response to a database query that includes a set of electronic records (e.g., a plurality of electronic records associated with different patients). Some of the electronic records received in the database query may not be needed by the care gap and efficacy analytics engine 140 or may be distracting to the task of identifying care gaps in patient data. Accordingly, the database interface instructions 132 and/or care gap and efficacy analytics engine 140 may be configured to utilize the electronic record filter 136 to reduce the number of electronic records received response to the database query before the care gap and efficacy analytics engine 140 begins processing the data.

The care gap and efficacy analytics engine 140, when executed by the processor 120, may enable the server 116 to analyze data records received from the patient database 180, analyze the data records for common care gaps shared between a group of patients having a common value in a data field of the patient's corresponding data record, determine a common care gap exists for the group of patients, map the common care gap to the common value in the data field, and/or determine an efficacy of treatment for various patient groups. In some examples, the care gap and efficacy analytics engine 140 may be configured to build and utilize one or more care gap matrices 144 to assist with the analysis of patient data records and identify care gaps between certain groups of patients. Additional details of such matrices 144 are described in U.S. Pat. No. 6,802,810, the entire contents of which are hereby incorporated herein by reference.

The patient grouping engine 148, when executed by the processor 120, may enable the server 116 to group data records of various patients according to common value(s) in one or more fields of such data records. For instance, the patient grouping engine 148 may group patient data records based on common ailments, common treatments, common prescriptions, common healthcare providers, common locations (e.g., state, city, ZIP code, etc.), common treatment histories, common genders, common age ranges, combinations thereof, and the like. In some examples, the patient grouping engine 148 may be leveraged by the care gap and efficacy analytics engine 140 for purposes of analyzing particular patient groups for common care gaps. In other words, the care gap and efficacy analytics engine 140 may receive a set of data records from the database interface instructions 132 and group patients in the received set of data records according to one or more shared attributes. Once grouped, the care gap and efficacy analytics engine 140 may analyze the data records for the group of patients and attempt to identify one or more common care gaps among the group or identify care gaps for one group as compared to other groups. Thus, the patient grouping engine 148 may be responsible for assisting the care gap and efficacy analytics engine 140 with grouping and re-grouping patient data based on common values in data fields of the patient's corresponding electronic data records.

The reporting engine 152, when executed by the processor 120, may enable the server 116 to generate one or more reports 184 that describe common care gaps identified by the care gap and efficacy analytics engine 140. The reporting engine 152 may be configured to generate reports 184 in various electronic formats, printed formats, or combinations thereof. Non-limiting examples of report 184 formats include HyperText Markup Language (HTML), electronic messages (e.g., email), documents for attachment to an electronic message, text messages, combinations thereof, or any other known electronic file format. The reporting engine 152 may also be configured to hide, obfuscate, redact, or remove PII data from a report 184 prior to transmitting the report 184 to a communication device 164. In some examples, the data obfuscation 156 may include aggregating patient data records to form aggregated patient data that does not include any PII for a particular patient or group of patients. Rather, the aggregated patient data generated by the data obfuscation 156 may include summaries of data records for patient groups, statistics for patient groups, or the like.

Again, the server 116 may also have one or more of its instruction sets (e.g., the care gap and efficacy analytics engine 140) executed as a neural network or similar type of artificial intelligence (AI) data structure. Furthermore, these neural networks may be capable of being dynamically trained and updated based on outputs of the server 116, based on responses received from users of communication devices 164, etc.

Figure 2:
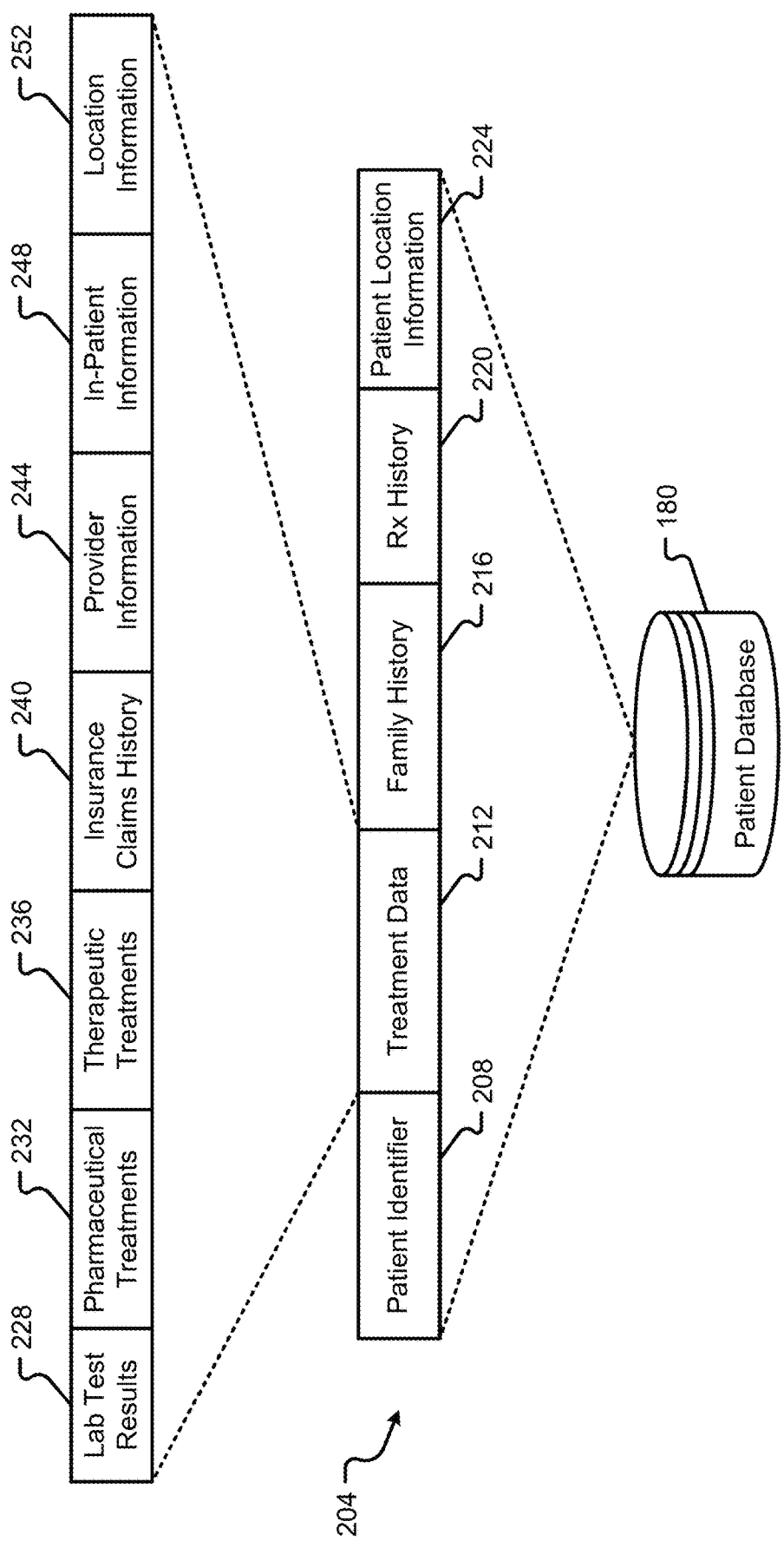
FIG. 2 is a block diagram depicting details of patient electronic data records in accordance with at least some examples of the present disclosure.

With reference now to FIG. 2, additional details of a patient database 180 and the type of data records that may be stored therein will be described in accordance with examples of the present disclosure. It should be appreciated that contents of the patient database 180 and the patient data records contained therein may be requested and analyzed by the server 116 for purposes of identifying common care gaps between patients and patient groups.

Illustratively, the patient database 180 is shown to have patient data records 204 stored thereon. The patient data records 204 may correspond to electronic data records that describe various aspects of a patient's health history and health outlook. The patient data records 204 may include a number of fields for storing different types of information to describe the patient's health history and health outlook. As an example, the patient data records 204 may include patient identifier 208 information, treatment data 212, family history information 216, a prescription history 220, and patient location information 224. The patient database 180 may correspond to any type of known database and the fields of the patient data records 204 may be formatted according to the type of database used to implement the patient database 180. Non-limiting examples of the types of database architectures that may be used for the patient database 180 include a relational database, a centralized database, a distributed database, an operational database, a hierarchical database, a network database, an object-oriented database, a graph database, a NoSQL (non-relational) database, etc.

The patient identifier 208 information may correspond to one or more data fields that are used to store patient data. As an example, the fields used to store the patient identifier 208 information may store certain types of PII data associated with a patient. As the name suggests, the patient identifier 208 can be used to store information that describes or identifies a patient (e.g., name, address, patient number, social security number, loyalty number, date of birth, etc.).

The treatment data 212 may include one or more data fields that are used to describe a patient's health history or journey. As some non-limiting examples, and as illustrated in FIG. 2, the treatment data 212 may include lab test results 228, pharmaceutical treatments 232, therapeutic treatments 236, insurance claims history 240, healthcare provider information 244, in-patient information 248, and/or location information 252. The lab test results 228 may include information that describes any labs the patient has completed and the results of those labs. The lab test results 228 may include text-based data as well as links to images (e.g., medical images, x-rays, MRIs, CAT scans, etc.) that were obtained for the patient.

The pharmaceutical treatments 232 and therapeutic treatments 236 may include information that describe the various treatments that have been prescribed or given to the patient. For example, the pharmaceutical treatments 232 may include information describing or identifying a prescribed medicament in a pharmaceutical treatment. The therapeutic treatments 236 may include information describing or identifying a non-pharmaceutical treatment (e.g., herbs, physical therapy, mental therapy, etc.) that has been given to a patient. In some examples, the pharmaceutical treatments 232 and/or therapeutic treatments 236 may be identified using a pre-defined healthcare code, treatment code, or the like.

The insurance claims history 240 may include information that describes the various insurance claims made by the patient. The insurance claims history 240 may be specific to a particular health insurance provider or may include insurance claims across a number of different health insurance providers. The insurance claims history 240 may identify insurance claims using predefined claims codes. The insurance claims history 240 in combination with the pharmaceutical treatments 232 and therapeutic treatments 236 may provide a holistic picture of a patient's health history or journey. However, as will be described herein, the information contained in these fields may only indicate the treatments and prescriptions that have actually been given to a patient. The care gap and efficacy analytics engine 140 may be configured to analyze these types of data across groups of patient data records 204 to help identify care gaps or provide clinical insights as to the types of prescriptions or treatments that a group of patients has not received as compared to another patient group, but perhaps should have received. As an example, the care gap and efficacy analytics engine 140 may be configured to monitor and track hundreds or thousands of health opportunities (e.g., common care gaps among a group of patients), allowing an identification of patients who may be in need of a prescription or treatment (e.g., Insulin). The information of many patient data records 204 can be rolled-up to a common field value among patient data records 204 (e.g., a common healthcare provider, a common location, a common claims history, etc.), thereby creating a path to unlocking a latent opportunity of unmet need in various ailments (e.g., diabetes). More specifically, but without limitation, utilization of the care gap and efficacy analytics engine 140 makes it possible to ascribe a large number of patients with gaps in care (e.g., in a certain area or with some common ailment) to an individual entity (e.g., a healthcare provider), so as to direct effort to that entity with the highest number of gaps.

Continuing the discussion of the treatment data 212, the provider information 244 may include information that describes one or more healthcare providers (e.g., doctors, chiropractors, mental therapists, physical therapists, life coaches, etc.) that are involved in providing healthcare services to the patient. Providers may be identified by a unique provider identifier or by groups of identifiers. For instance, a doctor may be identified by their name or by a medical license number assigned to the doctor by an appropriate healthcare agency.

The in-patient information 248 may include various types of information describing whether a patient has received inpatient care versus outpatient care. The in-patient information 248 may identify whether any of the insurance claims made by the patient were associated with inpatient care (e.g., care requiring admission to a hospital) or with outpatient care (e.g., care not requiring admission to a hospital).

The location information 252 may describe a location of treatment(s) provided to the patient. For instance, if a particular insurance claim was associated with a particular hospital, then the location information 252 may identify the hospital that provided the patient with care. Alternatively or additionally, the location information 252 may identify where certain prescriptions have been given, filled, or picked up by the patient. The location information 252 within the treatment data 212 may correspond to the location of or associated with a treatment provided to a patient. On the other hand, the patient location information 224 may identify a known location (e.g., residence address, ZIP code, city, state, etc.) of a patient. Thus, the patient location information 224 may be used to identify a location of patient regardless of where a treatment was provided to a patient, which is reflected in the location information 252 of the treatment data 212.

The family history 216 may include one or more data fields describing a patient's family health history. For instance, the family history 216 may include data links (e.g., database links, identifiers, hyperlinks, Universal Resource Locators (URLs), etc.) to other patient data records 204 belonging to family members of the patient. Alternatively or additionally, the family history 216 may include a description of the patient's family health history (e.g., whether there is a family history of certain health conditions).

The prescription history 220 may be included in the treatment data 212, but may be provided as a separate set of data fields since the prescription history 220 may include a greater or lesser number of data instances than those included in the treatment data 212. For example, a patient may have a number of prescriptions written for them, but less than all of those prescriptions filled. The treatment data 212 may be used to describe those prescriptions that have been filled by a pharmaceutical distribution entity (e.g., a pharmacy) whereas the prescription history 220 may describe additional prescriptions that were written for the patient, but which may not have been filled.

While details of the provider database 176 have not been described herein, it should be appreciated that certain aspects of a patient data record 204 may be stored in the provider database 176. A difference between the provider database 176 and the patient database 180 is that the provider database 176 may only be accessible to a healthcare provider of a patient and so may only include patient information that is specific to the healthcare provider that provided a particular treatment to the patient. Thus, the patient database 180 may serve as a better repository of information to describe an entire healthcare history or journey of a patient whereas the provider database 176 may provide a snapshot of a patient's healthcare history with respect to a particular healthcare provider. In some examples, the patient data records 204 stored in the patient database 180 may correspond to a collection or aggregation of patient data records 204 from various provider databases 176 as well as from other entities involved in the patient's healthcare delivery (e.g., a pharmaceutical distributor, a pharmaceutical developer, etc.).

Figure 3:
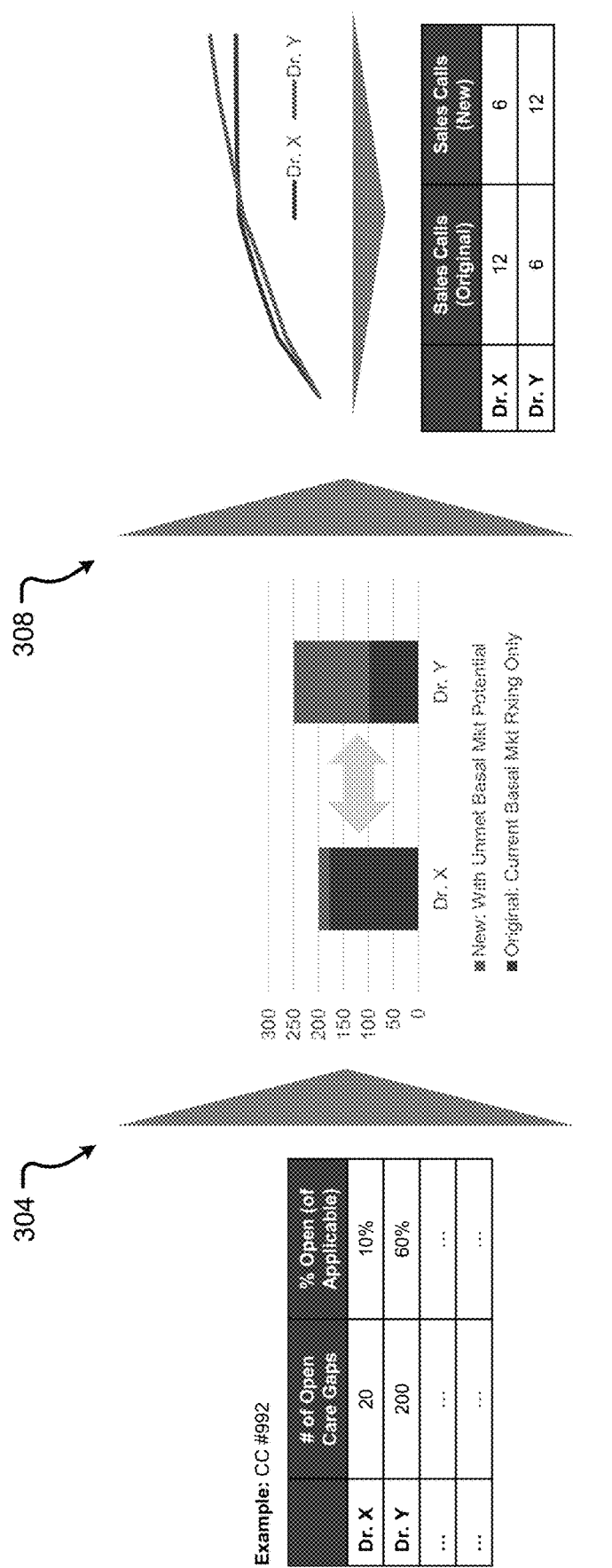
FIG. 3 illustrates a process for analyzing electronic data records to identify common care gaps therein and then act on the identification of the common care gap in accordance with at least some examples of the present disclosure.
Figure 4:
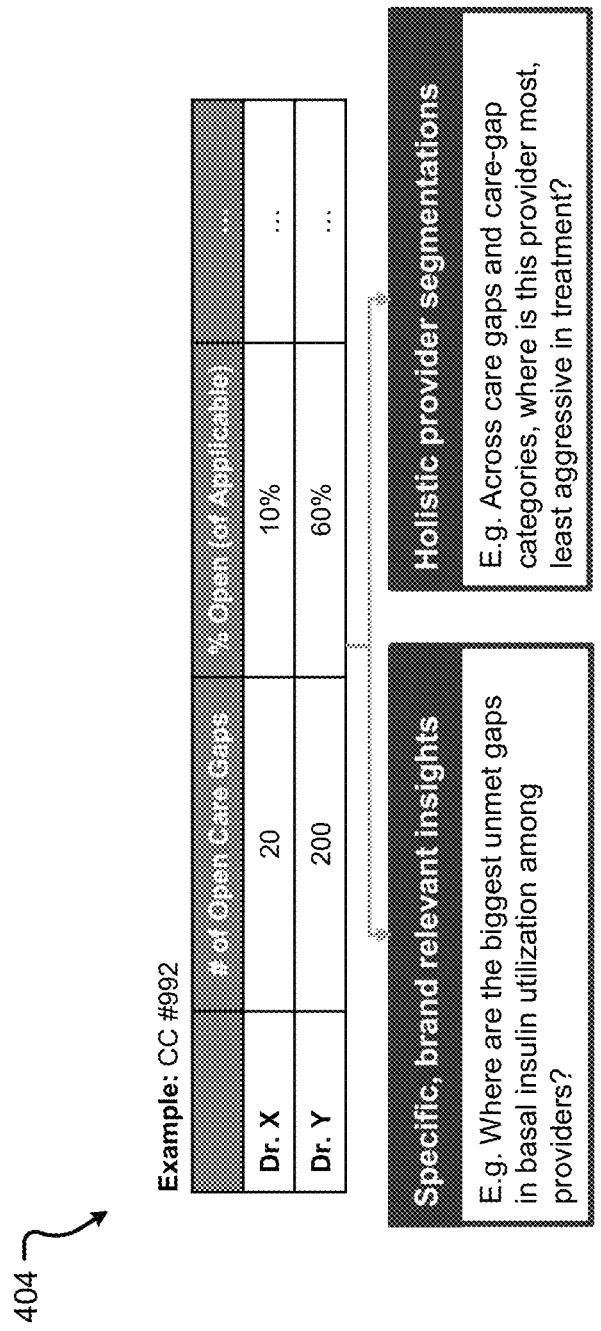
FIG. 4 illustrates care gaps identified for a particular treatment type in accordance with at least some examples of the present disclosure.
Figure 5:
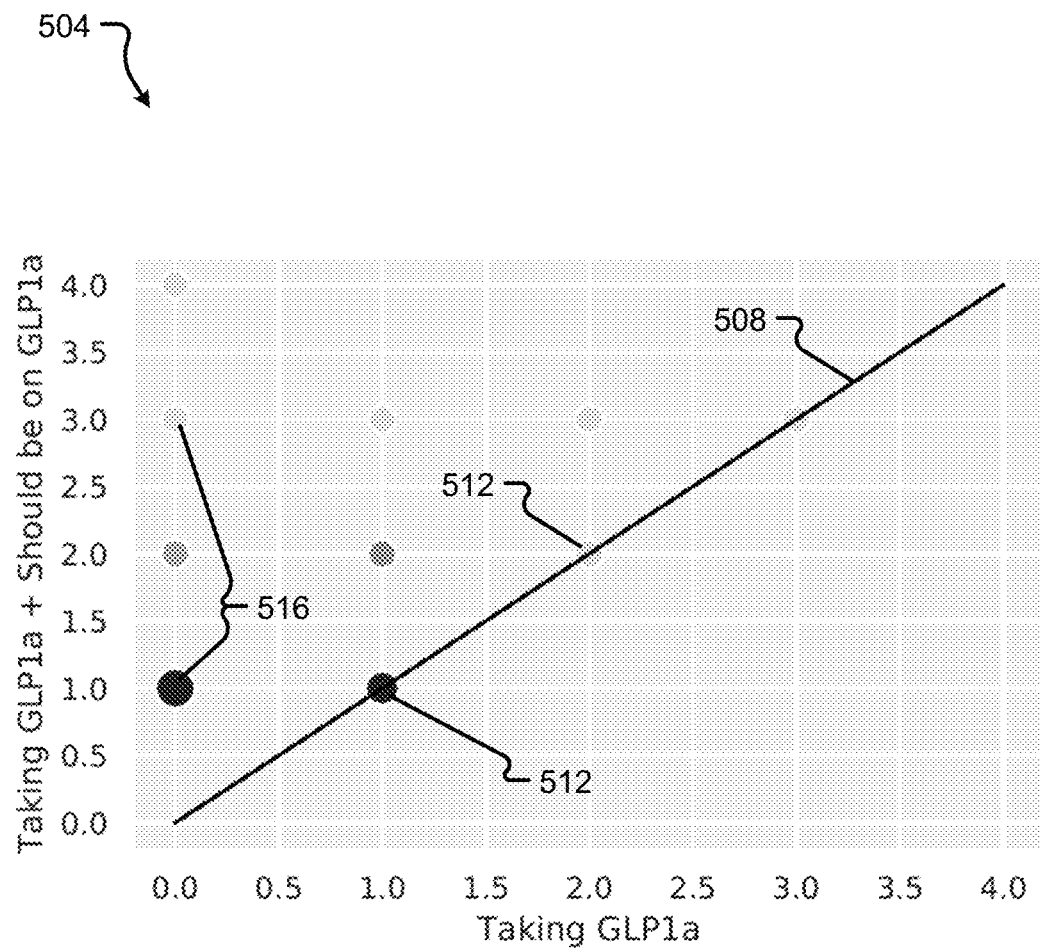
FIG. 5 illustrates a visualization of anomalous data occurrences in patient data in accordance with at least some examples of the present disclosure.

With reference now to FIGS. 3-5, certain examples of identifying common care gaps in treatment data 212 for a group of patient data records 204 will be described. The examples described herein are not intended to be limiting, but rather help provide a broader understanding of the capabilities of the care gap and efficacy analytics engine 140. FIG. 3 illustrates an example in which the care gap and efficacy analytics engine 140 is configured to aggregate care consideration insights for a particular care code (e.g., Diabetes with an elevated HbA1c, where Insulin therapy may be a consideration). The patient data records 204 for a number of patients having a common healthcare provider (e.g., Dr. X, Dr. Y, etc.) may be aggregated 304 to create a new information set. As will be described in further detail herein, patients' data records 204 may be grouped by other common values or combinations of common values (e.g., patient location information 224, insurance claims history 240, provider information 244, etc.).

The new information set may recast relative healthcare provider potential for impactable values. Said another way, if patient data records 204 are organized and grouped in an appropriate fashion, the care gap and efficacy analytics engine 140 may be configured to identify common care gaps from one group of patient data records 204 as compared to other groups of patient data records 204. In the example of FIG. 3, it can be seen that patient data records 204 associated with Dr. X have fewer care gaps than the patient data records 204 associated with Dr. Y. The identification of such common care gaps among a group of patients may be identified by the care gap and efficacy analytics engine 140 to generate 308 actionable data that describes actions another entity can take with respect to Dr. Y to help fill or address the common care gap associated with Dr. Y's treatment of patients. Results of identified common care gaps and the actionable data can be included in a report 184 and provided to an entity having the ability to provide treatments to fill the common care gap. To the extent that the patient data records grouped for Dr. X and Dr. Y are somewhat similar (e.g., similar in the treatment data 212) with the exception of being associated with a different healthcare provider, a conclusion can be drawn that further efforts to help Dr. Y change their practice can help the patients of Dr. Y receive valuable treatments that the patients are not currently receiving. In other words, the care gap and efficacy analytics engine 140 can help identify common care gaps for the purposes of reporting on such care gaps and enabling one or more entities to help fill the common care gaps.

FIG. 4 illustrates a non-limiting example of data 404 that may be included in a report 184 that is provided to an entity by the server 116. Specifically, the data 404 may include patient-level care considerations (e.g., common care gaps) aggregated at the healthcare provider level with meaningful summary statistics for clinical insights. Such insights may include identifications of the largest common care gaps for a particular healthcare provider (e.g., an identification of different treatments that are not being provided by the healthcare provider but are being provided by peer healthcare providers to similarly-situated patients), largest common care gaps for a location (e.g., an identification of different treatments that are not being provided to patients in a common location/ZIP code but are being provided to other similarly-situated patients in other locations), etc. As discussed above, the report 184 containing the actionable data 404 may be provided to one or many entities capable of helping fill the common care gap. Examples of such entities include healthcare providers, pharmaceutical developers, pharmaceutical distributors, patients themselves, healthcare agencies, and the like.

FIG. 5 illustrates a visual representation 504 of the aggregated patient data records and the analysis that can be performed by the care gap and efficacy analytics engine 140. In particular, the care gap and efficacy analytics engine 140 may be configured to identify common care gaps among patient data records 204 or groups of patient data records 204 by aggregating/grouping patient data records 204 using common values (e.g., healthcare provider information 244, location, treatment data 212, etc.), then searching for anomalous data occurrences 516 for the group of patients (and their data records) as compared to electronic data records of patients not in the group of patients. In the example of FIG. 5, for an individual healthcare provider, the care gap and efficacy analytics engine 140 may be configured to identify the number of patients on a particular medication, e.g., GLP-1a 512 and the number of patients (e.g., the anomalous data occurrences 516) that should be on the same treatment.

In the visualization of FIG. 5, an expectation line 508 may be drawn to represent points on the graph where data occurrences should fall to avoid a care gap, then any data occurrence not falling on or within a predefined threshold of the expectation line 508 can be identified as an anomalous data occurrence 516.

Figure 6:
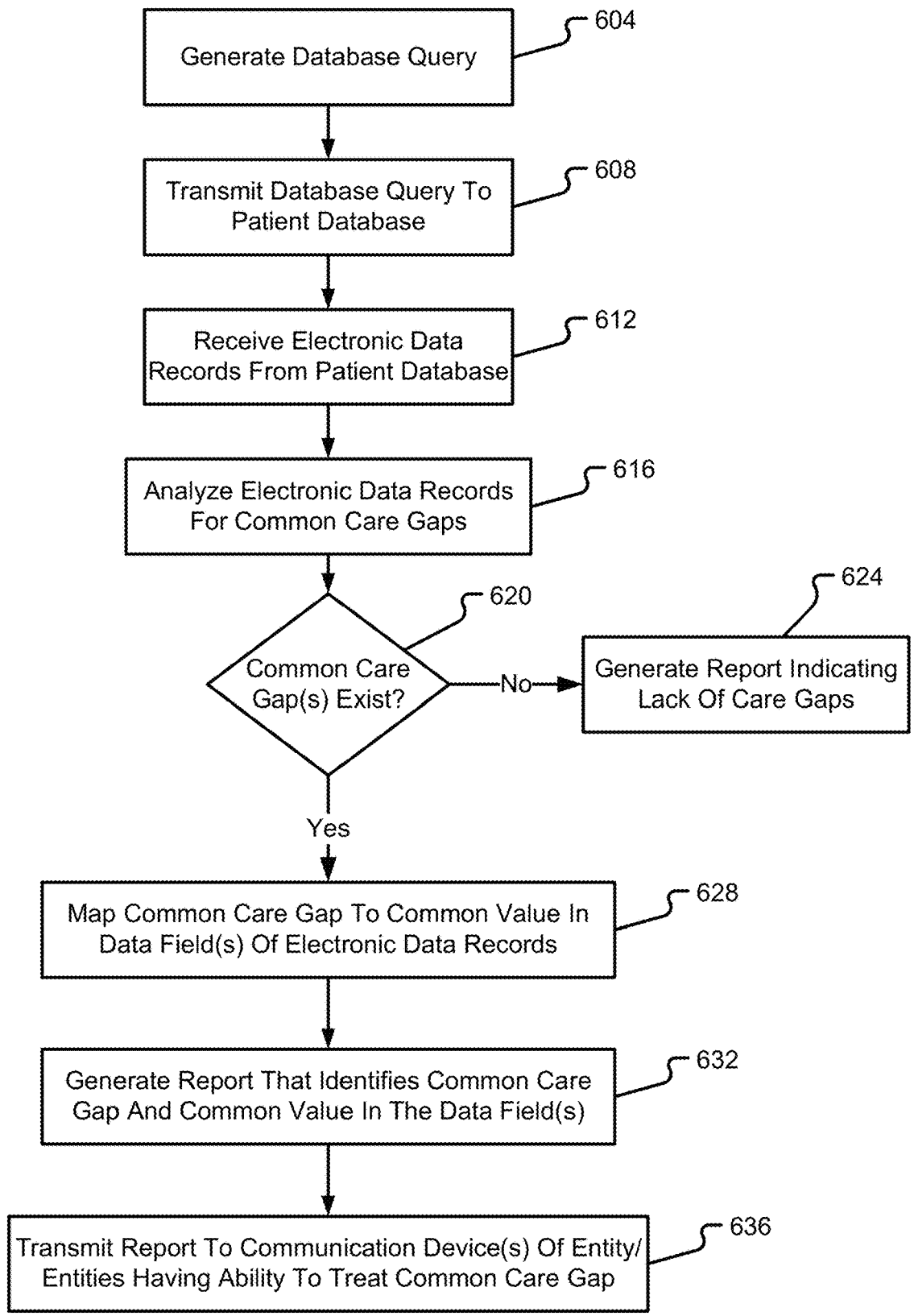
FIG. 6 is a flow diagram depicting a method of identifying and reporting on care gaps in accordance with at least some examples of the present disclosure.
Figure 7:
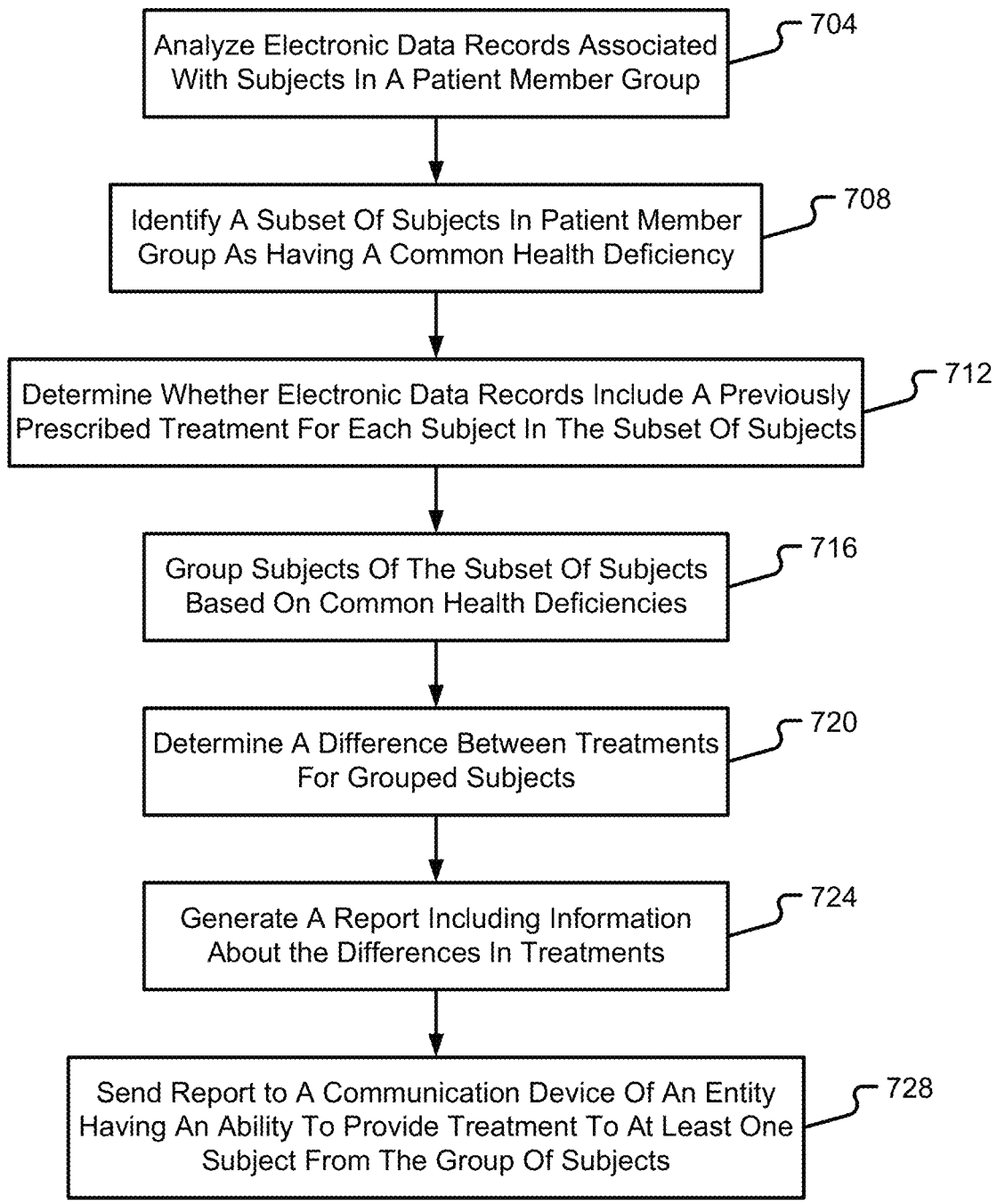
FIG. 7 is a flow diagram depicting another method of identifying and reporting on care gaps in accordance with at least some examples of the present disclosure.

With reference now to FIGS. 6-7, various methods of operating the systems 100 or components therein will be described. It should be appreciated that any of the following methods may be performed in part or in total by any of the components depicted and described in connection with preceding figures.

Referring initially to FIG. 6, a method of identifying and reporting on common care gaps will be described. The method begins with the database interface instructions 132 generating a database query (step 604). The database query may identify one or more common values in a data field of a patient's data record 204. The database query is transmitted to a patient database 180 (step 608), which returns a response to the query (step 612).

Upon receiving the response from the patient database 180, the server 116 continues by invoking the care gap and efficacy analytics engine 140 to analyze the electronic data records for common care gaps among the patient group that was represented in the data records 204 returned by the patient database 180 (step 616). Based upon the analysis performed in step 616, the care gap and efficacy analytics engine 140 will determine whether a common care gap exists (step 620) for the patient data records. If the query is answered negatively, then the reporting engine 152 may generate a report 184 indicating that no common care gaps were identified by the patient data records 204 that were grouped according to the common value used to generate the database query.

On the other hand, if the query of step 620 is answered positively, then the method proceeds by invoking the care gap and efficacy analytics engine 140 to map the common care gap to the common value in the data field(s) of the electronic data records (step 628). The mapping information may be provided to the reporting engine 152, which generates a report 184 identifying the common care gap(s) along with the common value used to group the patient data records 204 (step 632). The reporting engine 156 may optionally invoke the data obfuscation 156 to obfuscate or remove PII information from the report 184 prior to transmitting the report 184 to a communication device 164 of an entity having the ability to treat or address the common care gap (step 636).

With reference now to FIG. 7, another method of identifying and reporting on common care gaps will be described. The method begins by enabling the care gap and efficacy analytics engine 140 to analyze electronic data records 204 associated with subjects of a particular patient member group (step 704). The initial patient member group may be created according to a common value in patient data records 204 (e.g., a common healthcare provider, a common location, a common treatment data, etc.).

The method continues with the care gap and efficacy analytics engine 140 identifying a subset of subjects in the patient member group as having a common health deficiency (step 708). The common health deficiency may be identified based on common lab test results 228, common pharmaceutical treatments 232, common therapeutic treatments 236, common insurance claims history 240, common provider information 244, common in-patient information 248, common location information 224 or 252, combinations thereof, etc.

The care gap and efficacy analytics engine 140 may then determine whether the electronic data records include a previously prescribed treatment for each subject in the subset of subjects (step 712). The care gap and efficacy analytics engine 140 may then group the subjects of the subset of subjects based on a common health deficiency, which can be identified from the treatment data 212 of the patient data records 204 (step 716).

The care gap and efficacy analytics engine 140 may then determine a difference between treatments for the grouped subjects (step 720) and invoke the reporting engine 152 to generate a report 184 including information about the differences in treatments between the various patient groups (step 724). The report 184 may then be transmitted to a communication device 164 of an entity having an ability to provide treatment to at least one subject from the group of subjects (step 728).

A number of implementations have been described. Nevertheless, it will be understood that additional modifications may be made without departing from the scope of the inventive concepts described herein, and, accordingly, other examples are within the scope of the following claims.

What is claimed is:

1. A system, comprising:
a processor; and
computer memory coupled with the processor, wherein the computer memory comprises data stored thereon that enables the processor to:
transmit one or more database queries;
receive, in response to the one or more database queries, a plurality of electronic data records from a patient database, wherein each of the electronic data records in the plurality of electronic records comprises patient data and treatment data for a corresponding patient;
reduce, using an electronic record filter, a number of the plurality of electronic data records received from the patient database by filtering one or more electronic records from the plurality of electronic records received in response to the one or more database queries;
analyze the filtered electronic data records for common care gaps shared between patients in a group of patients having a common value in a data field of the treatment data for the corresponding patient;
determine, based on the analysis, a common care gap exists for each patient in the group of patients;
map the common care gap to the common value in the data field;
generate a report that identifies the common care gap and the common value in the data field; and
transmit the report to a communication device of an entity having an ability to provide treatment for the common care gap.

2. The system of claim 1, wherein the entity comprises a pharmaceutical developer and wherein the treatment comprises a pharmaceutical treatment.

3. The system of claim 1, wherein analyzing the electronic data records for common care gaps comprises applying a set of matrices to the electronic data records, wherein each matrix in the set of matrices contains a plurality of defined elements that incorporate medical treatment information for the patient from at least one healthcare provider, and wherein an identifier of the at least one healthcare provider corresponds to the common value in the data field.

4. The system of claim 3, wherein the common care gap comprises an anomalous data occurrence for the group of patients as compared to electronic data records of patients not in the group of patients.

5. The system of claim 4, wherein the anomalous data occurrence corresponds to an absence of a pharmaceutical treatment for patients in the group of patients while the pharmaceutical treatment is provided to patients outside of the group of patients.

6. The system of claim 3, wherein the common care gap corresponds to a gap in a pharmaceutical treatment, wherein the treatment data comprises an identifier of a prescribed medicament in the pharmaceutical treatment, and wherein the entity comprises a pharmaceutical developer.

7. The system of claim 1, wherein the report comprises a data file that aggregates the electronic data records for the patients in the group of patients and wherein the report anonymizes the patient data to remove sensitive information prior to transmitting the report.

8. The system of claim 1, wherein the electronic data records comprise a plurality of data fields describing the treatment data, wherein the plurality of data fields include a laboratory test results data field, a prescription drug data field, a health plan claims data field, a provider data field, and an in-patient information data field.

9. The system of claim 8, wherein the provider data field corresponds to the data field having the common value and wherein the common value comprises an identifier of the entity.

10. The system of claim 9, wherein the plurality of data fields further include a location data field, wherein the location data field corresponds to the data field having the common value, and wherein the common value comprises an identifier of a geographic area.

11. The system of claim 1, wherein the one or more database queries comprises a database query including at least one of an identifier of the entity, an identifier of a prescription drug, and a location identifier, and wherein the group of patients correspond to patients that comprise an electronic data record that satisfies the database query.

12. A method of identifying and reporting on care gaps, the method comprising:
transmitting one or more database queries;
receiving, in response to the one or more database queries and from a patient database, a plurality of electronic data records comprising patient data and treatment data for a corresponding patient;
reducing, using an electronic record filter, a number of the plurality of electronic data records received from the patient database by filtering one or more electronic records from the plurality of electronic records received in response to the one or more database queries;
analyzing, with a processor, the filtered electronic data records for common care gaps shared between patients in a group of patients having a common value in a data field of the treatment data for the corresponding patient;
determining, with the processor and based on the analysis, that a common care gap exists for each patient in the group of patients;
mapping, with the processor, the common care gap to the common value in the data field;
generating, with the processor, a report that identifies the common care gap and the common value in the data field; and
causing the report to be transmitted to a communication device of an entity having an ability to provide treatment for the common care gap.

13. The method of claim 12, wherein the entity comprises a pharmaceutical developer and wherein the treatment comprises a pharmaceutical treatment.

14. The method of claim 12, wherein analyzing the electronic data records for common care gaps comprises applying a set of matrices to the electronic data records, wherein each matrix in the set of matrices contains a plurality of defined elements that incorporate medical treatment information for the patient from at least one healthcare provider, and wherein an identifier of the at least one healthcare provider corresponds to the common value in the data field.

15. The method of claim 14, wherein the common care gap comprises an anomalous data occurrence for the group of patients as compared to electronic data records of patients not in the group of patients.

16. The method of claim 15, wherein the anomalous data occurrence corresponds to an absence of a pharmaceutical treatment for patients in the group of patients while the pharmaceutical treatment is provided to patients outside of the group of patients.

17. The method of claim 14, wherein the common care gap corresponds to a gap in a pharmaceutical treatment, wherein the treatment data comprises an identifier of a prescribed medicament in the pharmaceutical treatment, and wherein the entity comprises a pharmaceutical developer.

18. The method of claim 12, wherein the report comprises a data file that aggregates the electronic data records for the patients in the group of patients and wherein the report anonymizes the patient data to remove sensitive information prior to transmitting the report.

19. The method of claim 12, wherein the electronic data records comprise a plurality of data fields describing the treatment data, wherein the plurality of data fields include a laboratory test results data field, a prescription drug data field, a health plan claims data field, a provider data field, and an in-patient information data field, wherein the provider data field corresponds to the data field having the common value and wherein the common value comprises an identifier of the entity.

20. A system, comprising:
a processor; and
a computer memory coupled with the processor, wherein the computer memory comprises data stored thereon that enables the processor to:
  receive, in response to one or more database queries, a plurality of heath data records from a patient database, wherein each of the plurality of heath data records comprises patient data and treatment data for a corresponding patient;
  reduce, using an electronic record filter, a number of the plurality of health data records received from the patient database by filtering one or more electronic records from the plurality of health data records received in response to the one or more database queries;
  analyze the filtered health data records associated with subjects in a patient member group for health deficiency indicators;
  identify, based on the analysis of the health data records, a subset of the subjects in the patient member group having a common health deficiency;
  determine whether the health data records include a previously prescribed treatment for each subject in the subset of the subjects in the patient member group, the previously prescribed treatment associated with the common health deficiency;
  group subjects of the subsets in the patient member group having a same previously prescribed treatment associated with the common health deficiency into discrete groups;
  determine a difference between treatments for each group of the discrete groups;
  generate a report including information about the difference between treatments; and
  send, across a communications network, the report to a communication device of an entity having an ability to provide treatment to at least one subject from at least one of the discrete groups.

* * * * *